(12) United States Patent
Gutermuth (10) Patent No.: US 11,504,225 B2
(45) Date of Patent: Nov. 22, 2022

(54) ARTIFICIAL DESCEMET CONSTRUCT

(71) Applicant: FRAUNHOFER-GESELLSCHAFT ZUR FÖRDERUNG DER ANGEWANDTEN FORSCHUNG E.V., Munich (DE)

(72) Inventor: Angela Gutermuth, Aachen (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 598 days.

(21) Appl. No.: 15/561,417

(22) PCT Filed: Feb. 26, 2016

(86) PCT No.: PCT/EP2016/054101
§ 371 (c)(1),
(2) Date: Sep. 25, 2017

(87) PCT Pub. No.: WO2016/150652
PCT Pub. Date: Sep. 29, 2016

(65) Prior Publication Data
US 2018/0104046 A1    Apr. 19, 2018

(30) Foreign Application Priority Data
Mar. 26, 2015    (DE) .......................... 102015205534.5

(51) Int. Cl.
*A61F 2/14* (2006.01)
*A61L 27/38* (2006.01)
(Continued)

(52) U.S. Cl.
CPC .............. *A61F 2/142* (2013.01); *A61L 27/24* (2013.01); *A61L 27/3604* (2013.01);
(Continued)

(58) Field of Classification Search
CPC .... A61F 2/142; A61F 2240/001; A61L 27/24; A61L 27/3604; A61L 27/50;
(Continued)

(56) References Cited

U.S. PATENT DOCUMENTS

2005/0214259 A1   9/2005   Sano et al.
2007/0238173 A1   10/2007  Yamagami et al.
(Continued)

FOREIGN PATENT DOCUMENTS

CN    101014375 A    8/2007
CN    101333542 A    12/2008
(Continued)

OTHER PUBLICATIONS

English Translation of the International Preliminary Report on Patentability (Ch. I) for PCT/EP2016/054101, IB/Geneva, dated Sep. 26, 2017, incorporating the English Translation of the Written Opinion of the ISA, ISA/EP, Rijswijk, NL, dated Jul. 4, 2016.
(Continued)

*Primary Examiner* — Jerrah Edwards
*Assistant Examiner* — Christine L Nelson
(74) *Attorney, Agent, or Firm* — Harness, Dickey & Pierce, P.L.C.; Stephen T. Olson (57) ABSTRACT

A structured artificial construct that allows corneal endothelium to be regenerated from isolated cells outside the human or animal body is provided. The structured artificial construct is formed from a dome-shaped base body with a honeycomb structure formed in a concave side of the base body. Methods for generating the structured artificial construct are also provided.

17 Claims, 2 Drawing Sheets

(51) Int. Cl.
  *A61L 27/50* (2006.01)
  *A61L 27/24* (2006.01)
  *A61L 27/36* (2006.01)
  *C12N 5/079* (2010.01)

(52) U.S. Cl.
  CPC .......... *A61L 27/3834* (2013.01); *A61L 27/50* (2013.01); *C12N 5/0621* (2013.01); *A61F 2240/001* (2013.01); *A61L 2430/16* (2013.01); *C12N 2506/1384* (2013.01); *C12N 2533/54* (2013.01); *C12N 2535/00* (2013.01); *C12N 2537/00* (2013.01)

(58) Field of Classification Search
  CPC .............. A61L 2430/16; C12N 5/0621; C12N 2506/1384; C12N 2533/54; C12N 2535/00; C12N 2537/00
  See application file for complete search history.

(56) References Cited

U.S. PATENT DOCUMENTS

| | | |
|---|---|---|
| 2008/0026030 A1 | 1/2008 | Kinoshita et al. |
| 2009/0222086 A1 | 9/2009 | Lui et al. |
| 2009/0232772 A1 | 9/2009 | Amano et al. |
| 2010/0215717 A1 | 8/2010 | Soker et al. |
| 2012/0282318 A1 | 11/2012 | Nishida et al. |
| 2013/0244328 A1 | 9/2013 | Yokoyama et al. |
| 2015/0374881 A1 | 12/2015 | Yamagami et al. |

FOREIGN PATENT DOCUMENTS

| | | | | |
|---|---|---|---|---|
| CN | 101433478 A | | 5/2009 | |
| CN | 101638635 A | | 2/2010 | |
| CN | 101745152 A | | 6/2010 | |
| CN | 102532440 A | | 7/2012 | |
| EP | 1835023 A1 | * | 9/2007 | ......... A61L 27/3839 |
| EP | 1988152 A1 | * | 11/2008 | ............ C12M 23/12 |
| JP | 2002078723 A | | 3/2002 | |
| JP | 2004024852 A | | 1/2004 | |
| JP | 2005229869 A | | 9/2005 | |
| JP | 2006187281 A | | 7/2006 | |
| JP | 2009511197 A | | 3/2009 | |
| JP | 2012125207 A | | 7/2012 | |
| WO | WO 2017/051252 | * | 5/2007 | |
| WO | 2007097120 A1 | | 8/2007 | |
| WO | 2011021706 A1 | | 2/2011 | |
| WO | 2014104366 A1 | | 7/2014 | |

OTHER PUBLICATIONS

International Search Report for PCT/EP2016/054101, ISA/EP, Rijswijk, NL, dated Jul. 4, 2016, with English translation.
Kopsachilis, N. et al.: "Descemet's membrane substrate from human donor lens anterior capsule", Clinical and Experimental Ophthalmology, 2012, 40, S. pp. 187-194.
Espana, E. et al.: "Long-term follow-up of a supradescemetic keratoprothesis in rabbits: an immunofluorescence study", 2011, 249, S. pp. 253-260.
Written Opinion of the ISA for PCT/EP2016/054101, ISA/EP, Rijswijk, NL, dated Jul. 4, 2016.
Chinese Office Action (in English) dated Jan. 15, 2020 in corresponding Chinese Application No. 201680018119.9.

* cited by examiner

ARTIFICIAL DESCEMET CONSTRUCT

CROSS REFERENCE TO RELATED APPLICATIONS

This application is a 371 U.S. National Stage of International Application No. PCT/EP2016/054101, filed Feb. 26, 2016, which claims the benefit of and priority to German Patent Application No. 10 2015 205 534.5, filed Mar. 26, 2015. The disclosures of the above applications are incorporated herein by reference.

FIELD

The present invention relates to methods and means for producing corneal endothelial tissue of the mammalian eye, and provides a structured artificial construct which enables the formation of a corneal endothelium from isolated cells outside the body.

BACKGROUND

The transparency of the cornea of the eye is essential for proper vision. Above all, it requires an intact endothelial tissue (corneal endothelium). This single-layered endothelium at the back of the cornea is in direct contact with a cell-free basal membrane, the so-called Lamina limitans posterior descementi or Descemet membrane, which delimits is from the main layer of the cornea, the stroma. The Descemet membrane of the healthy cornea consists essentially of type VIII collagen and laminin. It has a regular spatial structure, which corresponds to the structure of the cells of the endothelium. The endothelium actively drains the stroma across the Descemet membrane, preventing water retention and edema formation, and thus opacity of the cornea.

Human corneal endothelial cells arrest in the GI-phase and show only limited ability to proliferate in vivo. Their inability to divide implies that in the case of corneal injury, be it due to inflammatory processes or by mechanical trauma, but also due to natural aging processes, an irrevocable destruction of the endothelium may incur and, in the worst case, vision may be completely lost due to corneal opacity. Although dead endothelial cells are replaced by neighbors, they become larger and migrate into gaps in order to ensure the tightness and function of the endothelium. However, this repair mechanism is very limited.

Endothelial cell loss in the cornea can be cured by medical measures to only limited extend. An often used method is the substitution of the entire damaged cornea with a donor cornea in the so-called perforating keratoplasty. However, clinical complications often occur, which cause a lack in or a reduced rehabilitation of the eye, such as chronically dry eyes, corneal vascularization and, in the worst case, a rejection of the foreign donor material.

Besides to this total substitution, methods have now been established in which, after local removal of the damaged endothelium together with its Descemet membrane (Descemetorhexis), a lamellar transplant consisting of a corneal endothelium and attached Descemet membrane, and a small portion of posterior stroma, is introduced from a donor cornea into the anterior chamber of the recipient. Through this specific transplantation, the usual risks of a transplant and the side effects of the operation are reduced against a total transplant. However, there are still further technical problems that have not yet been overcome.

A general problem with such allogeneic transplants of corneal tissue is the loss of endothelial cells. The preparation technique at the donor eye, the manner of storage and the nutrient medium used, the transport and ultimately the perioperative handling of the donor tissue always result in a more or less pronounced loss of endothelial cells in the transplant. In addition to the immunoreactive degeneration of the foreign tissue, these factors can lead to a primary transplant failure as well, rendering the transplanted endothelial tissue non-functional and no rehabilitation takes place.

SUMMARY

The object of the invention is to overcome such disadvantages in the clinical repair of corneal endothelial tissue. In particular, the known disadvantages of allogeneic transplants, but also, in particular, the problem of cell death of endothelial cells in explanted donor tissue, should be reduced.

The invention provides methods and means for producing a novel biological endothelial implant which overcome the above-described disadvantages of known transplants: a corneal endothelial tissue which can be produced de novo in tissue culture from isolated cells on the basis of a novel artificial Descemet membrane.

The inventors surprisingly found that isolated omnipotent or pluripotent stem cells can be stimulated by a special artificial construct, that is specifically replicating the Descemet membrane present in the healthy cornea, to form a functional corneal endothelial tissue de novo with high cell density, which together with the inventive artificial Descemet construct itself can be implanted into the patient's eye to completely replace the function of the lost corneal endothelium.

The invention thus provides for an artificial Descemet construct which is particularly suited to support or enable a mechanotransductive differentiation of biological cells, particularly of pluripotent or omnipotent cells, to form a corneal endothelial tissue in vitro.

Without wishing to be bound by theory, after seeding of isolated cells on to the Descemet construct according to the invention, a mechanotransductive differentiation of these cells, and thus the formation of functional corneal endothelial tissue, takes place. Thereby, autologous cells, especially pluripotent or omnipotent cells, of the recipient itself can be used. Thus, an artificial corneal implant can be provided, which consists of the recipient's own cells, and wherein, by suitable cultivation measures in the in vitro cultivation of the tissue, the cell number and cell density can be chosen such that a possible peri- or postoperative cell death can be compensated for. After transplantation, the function of the transplanted endothelial tissue is permanently retained and a complete permanent rehabilitation can be achieved.

According to the invention, the Descemet construct consists of a substantially spherical dome-shaped basic body, a honeycomb structure being formed on the concave side (cavity) of this basic body on the surface thereof. The spatial honeycomb patterning of the surface of the base body can be produced by suitable microstructuring methods.

In the context of this invention, "calotte-shaped" or "spherical" is not exclusively a spherical section in the narrower sense, but also encompasses forms and shapes corresponding essentially to this form, including half-shell or semi-dome shapes, such as sections or caps of rotational ellipsoids, rotational paraboloids, as well as intermediate forms thereof. According to the invention, the artificial Descemet construct particularly has a shape which corresponds to the form of the cornea to which the implant formed by or with the construct is to be implanted.

In particular, the honeycomb structure as such is designed composed of repetitive geometric base elements or honeycombs, which are preferably arranged without a gap in the form of a honeycomb, each imaginary base element having a central recess and lateral webs which delimit this towards the neighboring base elements. Preferably, the web height, and thus the depth of the central recess, is 0.3 to 1 µm. The web width is preferably 1 to 8 µm. The width of the central recess enclosed by these webs is preferably from 10 to 20 µm.

Preferably, the basic elements each have a hexagonal basic shape and thus form a classical honeycomb structure. In alternative embodiments, the basic form of the repetitive basic elements is circular or substantially circular. In an alternative variant, the basic shape is essentially rectangular or square. In an alternative variant, the basic shape is generally polygonal. Preferably, polygons of different number of corners, preferably with five to nine corners, alternate. These honeycomb structures are particularly preferably composed of hexagons and pentagons.

In a particular variant, the honeycomb structure is strictly regular, that is to say it is constructed from essentially uniform and preferably essentially the same basic elements. In an alternative and preferred variant, the honeycomb structure is irregular. That is, the imaginary basic elements each have a different size and/or different individual shape, the sizes of the basic elements being preferably (quasi-) stochastically distributed in the honeycomb structure. The mean size of a group of 6 to about 24 underlying base elements is thereby kept constant. The afore-mentioned preferred size ranges are not exceeded in this case.

The webs, that is to say side walls of the basic elements, are preferably each arranged preferably perpendicular to the basic plane of the structured surface of the base body. In an alternative variant, the side walls of the base element converge conically to the bottom of its recess. For this purpose, it is particularly provided that the thickness of the side walls increases towards the bottom of the depression. The recess thus encloses the shape of a polygonal pyramid stump, or, in the case of a substantially circular cross-section, that of a truncated cone.

In one variant, a circumferential edge projecting from the half-shell is provided. This does not need to be structured. It is used to facilitate the handling of the Descemet construct during microstructuring and on the other hand during the use of the Descemet construct in cell cultivation. If desired, the border can be separated off as part of an implant after completion of the cell culture phase or before implantation of the Descemet construct.

In a preferred embodiment, the Descemet construct according to the invention contains a biological or biocompatible polymer and preferably consists entirely thereof. The biological or biocompatible polymer is preferably mechanically elastic and flexible. In an alternative variant, it is essentially inelastic but flexible.

For the selection of biological or biocompatible polymers, it is relevant that when the Descemet construct is implanted into the eye as part of an in vitro implant, it can postoperatively replace the physicochemical function of a native Descemet membrane. This includes, in particular, the permeability (passive diffusion) to pass aqueous humor from the stroma towards the actively pumping endothelial tissue. This diffusion is particularly made possible by selecting the polarity of the material components and/or by means of porous or perforated structures (molecular sieve).

In addition, it is provided that the artificial Descemet construct is partially or completely resorbable after implantation. A residual structure, which assumes the function of the native basal membrane, remains in this case, whereas materials for the particularly mechanical stabilization of the implant in the Descemet construct are resorbable immediately after implantation. It is also provided that a basal membrane forms out of the artificial Descemet construct postoperatively.

It is further provided that the mechanical properties of the biological or biocompatible polymer are selected in such a way that the mechanical properties of a native Descemet membrane are achieved. In particular, a mechanical stiffness of the Descemet construct is required in order to enable the mechanotransductive formation of corneal endothelial tissue de novo from isolated cells in vitro in the tissue culture and, on the other hand, to ensure adequate stability during implantation into the recipient eye, peri- and postoperatively. In a variant, the mechanical properties of the construct are altered during in vitro cultivation and/or postoperatively. For this purpose, a composition is selected from a plurality of components which exhibit different resorption or interact with the endothelial cells.

The biocompatible polymer(s) of the construct may be fully or partially of synthetic origin. They can be functionalized in a known manner and in particular may be coupled with adhesion-supporting proteins or peptides.

The polymer preferably comprises or preferably consists of a collagen or a collagen mixture. Preferred collagen is collagen type I and/or type II. Particular preference is given to collagen type VIII and/or type IV. Alternatively, mixtures of these are preferred. Preferably laminin is contained in addition. Preferably fibronectin is contained in addition. Biochemically, the native Descemet membrane consists mainly of collagen type IV and VIII, fibronectin and laminin. It is preferably provided that these extracellular matrix components are preferably produced according to standardized methods and preferably recombinantly. The mixing ratio of the components is adjusted such that the pore size in the artificial construct and thus the diffusion potential of the native Descemet membrane is achieved. A collagen or collagen mixture which has a natural nanostructure is preferably used. This enhances the mechanotransductive effect of the microstructuring of the Descemet construct according to the invention and accelerates and stabilizes the differentiation of the isolated cells into an endothelial tissue.

Additionally or alternatively, the biomaterial contains or consists of recombinantly produced proteins known from the infantile or adult native Descemet membrane of the animal or human body. The proteins may be xenogeneic or allogeneic. Recombinantly produced human collagen or collagen mixtures are preferred. Alternatively or additionally, the Descemet construct contains or consists of silk protein. In one variant, the construct contains biocompatible polymers of non-biological origin or consists exclusively of them.

In an alternative variant, the material of the Descemet construct is synthetic polymers and elastomers such as silicone elastomer or PMMA, polyethylenes, polyamides, PVA, as well as functionalized polymers, copolymers and copolymers. Particular preference is given to thermosensitive or thermoreactive polymer, in particular an N-isopropylacrylamide, also modifications or derivatives thereof, as well as N,N-diethylacrylamide (PDEAAm), N-vinylcaprolactam (PVCL) and the like.

Preferably, at least the surface of such a synthetic polymer is functionalized, for example by coating or chemical or physical treatment of the polymer in order to achieve compatibility with biological cells cultured thereon in a manner known per se. The polymer may be linked by a plasma sterilization process with laminin and/or fibronectin or else cell adhesion protein via hydrogen bonding. The polymer can be prepared by chemical coupling (e.g. EDC/NHS reaction) can be covalently coupled to an adhesion promoting protein (see above).

According to the invention, the Descemet construct is produced by means of microstructuring. These are preferably selected from photolithographic structuring methods, photolytic ablation, micromechanical ablation, as well as molding and shaping.

Microstructuring is preferably carried out by means of so-called ablation processes to chisel out the desired honeycomb structure by material removal. Laser-based methods (photolytic ablation) are preferred. In the case of direct structuring by laser, a focused laser beam is directed onto the component surface, whereby the energy of the incident laser radiation is converted into thermal energy by absorption near the edge. The efficiency of this conversion is determined by the degree of absorption of the material as a function of laser wavelength, surface roughness, angle of incidence and temperature. On contrast, the radiation energy may directly break chemical bonds. Alternatively or additionally, the removal of material includes a phase transition in the material from solid to liquid and finally to gaseous. In all cases, in the area of the focused laser beam material is removed in the form of particles and/or material melts. In the case of pulsed lasers, this produces in particular a single geometry per laser pulse, mainly in the form of a rotational paraboliod ("well").

The generation of adjacent structures is effected by suitable movement of the laser beam over the workpiece surface. This is preferably implemented with the aid of so-called laser scanners, which comprise one or more movable mirrors, which are operated via fast motors. The quality of the removal in terms of achievable structure size, structure accuracy and accuracy can be selected by suitable choice of the laser source. Decisive are the wavelength of the laser light, the output power (in the case of pulsed lasers the single pulse energy) and the beam quality of the source.

Preferred alternative microstructuring methods are mechanical chip-removing processes, particularly diamond micro-lathing with microcrystalline tools. Structural dimensions in the sub-micrometer range may be produced by a combination of special machine technology and highly sharp tools only. Structural dimensions in this range are based on so-called ultra-precision technologies. For this purpose, monocrystalline diamond tools are preferred which, by virtue of their hardness and sharpness, and by means of their precise cuts, enable the desired structures to be produced. The production of ultra-precise components in this lathing process is preferably restricted to the production of rotationally symmetrical surfaces. Extending to so-called non-circular machining, it is also possible to alternatively produce surfaces and structures which are not symmetrical to a rotational axis.

Alternatively, preferred approaches for microstructuring the Descemet construct are so-called generating methods, wherein the honeycomb structure according to the invention is formed by local material build-up or material curing on a base body after application of material. Preferred methods are two-photon lithography, interference lithography and grayscale lithography.

Two-photon lithography (2PL) is based on the physical effect of two-photon absorption (2PA) and allows three-dimensional structures to be fabricated at a lateral resolution of 150 nm and an axial resolution of 400 nm. The widened beam of a femtosecond fiber laser with a wavelength of 780 nm is coupled into an inverted microscope lens and thus is focused into a liquid photosensitive polymer. Since the laser is focused and pulsed, the focus intensity is high enough to allow two-photon absorption within the focus. In the corresponding region, instead of infrared radiation, ultraviolet radiation with a wavelength of 390 nm is emitted. The liquid photopolymer as a constituent of the basic body of the construct only crosslinks during exposure by the energetic UV radiation, so that the liquid polymer cures on the base body in the region in which two-photon absorption takes place and thus the honeycomb structure can be formed.

In the case of interference lithography, the two-beam or multi-beam interference is used to image and store the corresponding interference pattern in a light-sensitive surface. For this purpose, a laser beam (argon ion laser) is expanded and (e.g. by a beam splitter cube) into two partial beams. These are superimposed with mirrors (plane or concave mirrors) at a certain angle so that a striped pattern with a certain lattice constant arises as a function of this angle as well as the wavelength used. A honeycomb structure can be formed by repeated application, especially after rotation of the base body.

Greyscale lithography is based on the exposure of a mask whose pattern is stored by the exposure in a photosensitive polymer. Different depths of structure are realized by different gray shades on the mask. Behind the mask, an intensity distribution is formed corresponding to the grey tone distribution on the mask. Using a positive resist, the structure is deepest where the intensity is highest. For negative resists this relationship is reversed.

Particularly preferred for the production of a biological or biocompatible and implantable Descemet construct are embossing or casting processes and combinations thereof, wherein a negative form (template) of the desired Descemet construct is first produced by means of the above-mentioned ablative or generating methods in a, preferably polymeric, material, and subsequently the Descemet construct itself is produced from biological or biocompatible polymer by means of casting and/or embossing as a positive mold on the previously produced die. By means of this preferred two-stage process, microstructuring can also take place on biological or biocompatible polymers which as such are not directly applicable in physical microstructuring processes. Molding is particularly intended for all biomaterials which are subject to a curing or polymerisation process, i.e. a gel-like or solid state is obtained out of a liquid, pourable aggregate state by curing. In the molding process, it cures on the negative mold (casting) or the negative mold is pressed into the material (embossing). In addition to pure biomaterials of biological origin, the synthetic polymers described herein are also provided for molding.

The invention further provides a process for the production of an artificial Descemet construct, comprising at least the steps: (1.) Providing a polymeric base body, and (2.) forming a three dimensional honeycomb structure in a surface of the base body by means of a microstructuring method. Said method is preferably selected from: photolithographic structuring, photolytic ablation, micromechanical ablation, molding and shaping.

Preferably, the step of forming the spatial honeycomb structure includes the following: (2.1) Creation of a negative form (die) of the honeycomb structure by means of a microstructuring process and then (2.2) forming the final honeycomb structure in a biocompatible or biological polymer by casting or embossing by means of the produced negative form.

According to the invention, the artificial Descemet construct described herein is used in a "tissue engineering" approach outside the human or animal body to regenerate an endothelial tissue from individual cells. The invention therefore also relates to the use of the artificial Descemet construct for the mechanotransductive differentiation of, in particular mesenchymal, precursor or stem cells into a corneal endothelial tissue in vitro.

The cells from which the corneal endothelial tissue is to be formed de novo according to the invention on the Descemet construct are preferably eukaryotic precursor cells, especially adult stem cells, embryonic stem cells, and induced pluripotent stem cells. Preferred are mesenchymal cells, particularly preferably mesenchymal stem cells. These are preferably isolated from tissue of the recipient. For this purpose, adult stem cells are preferably removed minimally invasively from autologous adipose tissue of the patient.

For in vitro differentiation, the cells are seeded on the structured surface of the Descemet construct according to the invention and cultivated there. The cell seeded density is preferably at least $5 \times 105/cm^2$. To support the differentiation of the cells in vitro, it is eventually also possible to apply known chemical factors, which support the mechanotransduction of the cells on the microstructured Descemet construct according to the invention. In particular, however, it is provided that the differentiation of the cells takes place exclusively by means of mechanotransduction on the microstructuring of the artificial Descemet construct according to the invention. The de novo corneal endothelial tissue obtained therefore is essentially unaffected by chemical or other physical differentiation factors, which on the one hand stabilizes the differentiation, on the other hand reduces the mortality of these cells or any de-differentiation also post-operatively.

The invention thus also relates to a method for the production of a de novo corneal endothelium implant from isolated biological cells, comprising the steps: (1) contacting isolated biological cells with the artificial Descemet construct, (2) culturing said cells on the Descemet construct, whereby differentiation of the cells takes place in endothelial cells of a corneal endothelium, and (3) obtaining of tissue differentiated to a de novo corneal endothelium with the Descemet construct according to the invention as an artificial Descemet membrane as the in vitro corneal endothelium implant.

Thus, in this variant, the artificial Descemet construct, together with the cells differentiated to an endothelium, is used as an implant for repairing endothelial defects on the cornea in patients. In this variant, the aforementioned biomaterials are preferred as material for the Descemet construct.

Another embodiment of the invention is the provision of the artificial Descemet construct together with the corneal endothelial tissue formed thereon as an in vitro tissue implant. The latter is implantable into the eye of a recipient, vertebrate eye, especially mammalian eye, especially human eye, to replace the function of a destroyed corneal endothelial tissue. The invention therefore also provides an in vitro implant containing corneal endothelial tissue, which is composed of isolated cells, and the artificial Descemet construct. The differentiated de novo corneal endothelial tissue, which adheres to the Descemet construct according to the invention, can be used as a prefabricated in vitro implant and transferred into the recipient eye by means of known surgical techniques, in particular the DMEK (Descemet membrane endothelial keratoplasty) or DMAEK (Descemet membrane automated endothelial keratoplasty).

The invention also provides a method for the production of a de novo corneal endothelium implant from isolated biological cells, comprising the steps: (1) contacting isolated biological cells with the artificial Descemet construct, (2) cultivating the cells on the Descemet construct, whereby differentiation of the cells into endothelial cells of a corneal endothelium takes place, (3) obtaining of tissue differentiated to a corneal endothelium de novo on the Descemet construct according to the invention, (4) detaching the corneal endothelial tissue from the Descemet construct and obtaining the isolated corneal endothelial tissue as the in vitro corneal endothelium implant.

In this alternative variant it is thus provided that, after differentiation of the cells seeded thereon to an endothelial tissue, it can be detached again from it, and to utilize the isolated endothelial tissue as an implant for the repair of endothelial defects on the cornea of patients.

The detachment of the endothelial tissue from the artificial Descemet construct can be carried out according to methods which are known from in vitro tissue culture. Such include the application of solvent enzymes, detergents, and the like. It is provided that the cells are treated with a gentle enzyme such as Accutase. Besides the destruction of adhesion proteins which mediate the adhesion of the endothelial cells to the substrate, it is necessary to prevent destruction of "tight junctions" between the endothelial cells, which else would impair the functional integrity of the tissue.

Alternatively or additionally, it is preferred that the surface of the Descemet construct is specifically coated or functionalized at least on the side of the contact with the endothelial cells to reduce the formation of adhesion factors and to facilitate detachment.

In a particularly preferred variant, the synthetic polymer of the Descemet construct is, alternatively or additionally, a thermosensitive or thermoresponsive polymer described herein, preferably a N-isopropylacrylamide. In such materials, adhesion or the detachment of the endothelial cells from the substrate, i.e. the Descemet construct, can be controlled via the temperature. For the detachment of the endothelial cells, the Descemet construct with the endothelial cells is preferably brought to a low temperature of about 20° C. or less after completion of the cultivation/differentiation phase. As a result, the thermosensitive substrate undergoes a change of state, which leads to the detachment of the endothelial tissue as a whole or largely supports this.

The present invention thus further provides the corneal endothelial tissue as such formed in vitro as the in vitro tissue implant. This is implantable into the eye of a recipient, vertebrate eye, especially mammalian eye, especially human eye, to replace the function of destroyed corneal endothelial tissue. The invention therefore also provides an in vitro implant consisting of the corneal endothelial tissue, which is composed of isolated cells de novo. The isolated de novo corneal endothelial tissue can be transferred into the recipient eye by means of known surgical techniques, in particular the DMEK (Descemet membrane endothelial keratoplasty) or DMAEK (Descemet membrane automated endothelial keratoplasty).

DETAILED DESCRIPTION

The invention is described in more detail with reference to the following figures and the examples for specific embodiments.

Figure 1A:
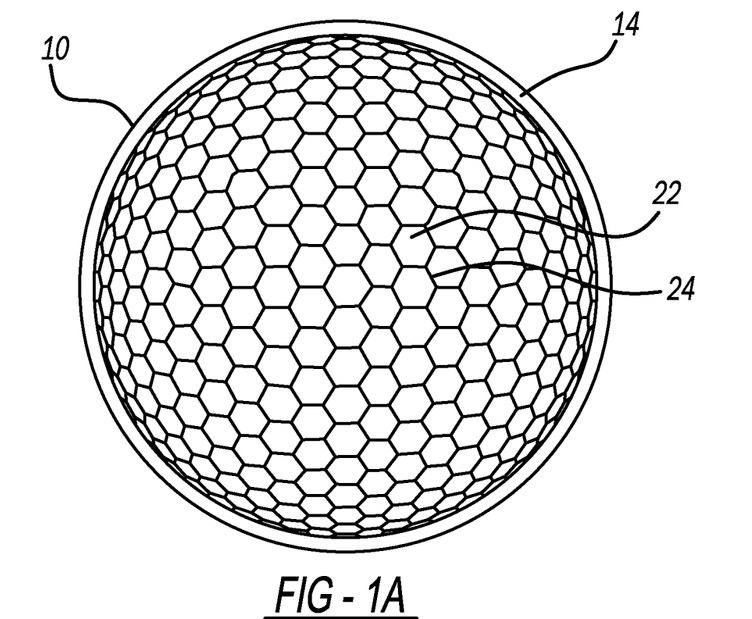
FIGS. 1A and 1B are illustrations of plan views of concave sides of dome-shaped Descemet constructs.
Figure 1B:
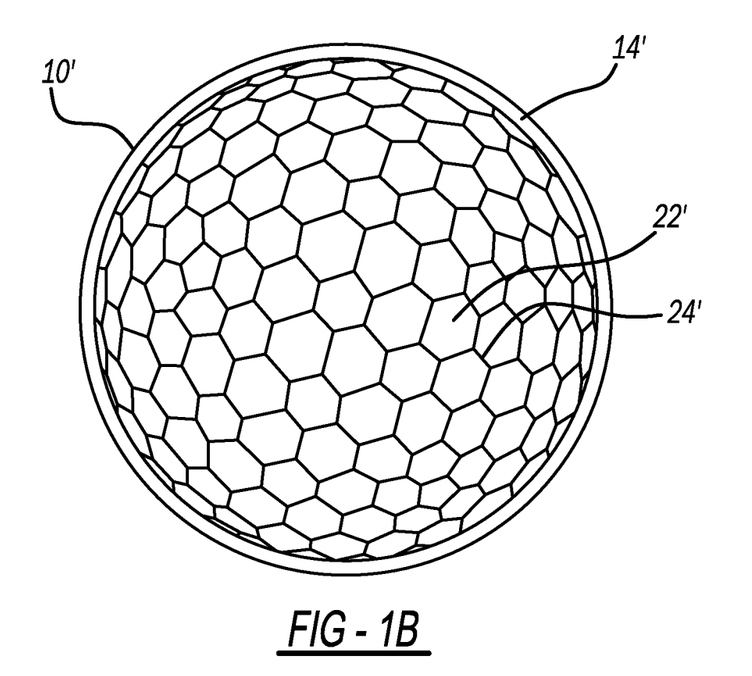
Figure 2A:
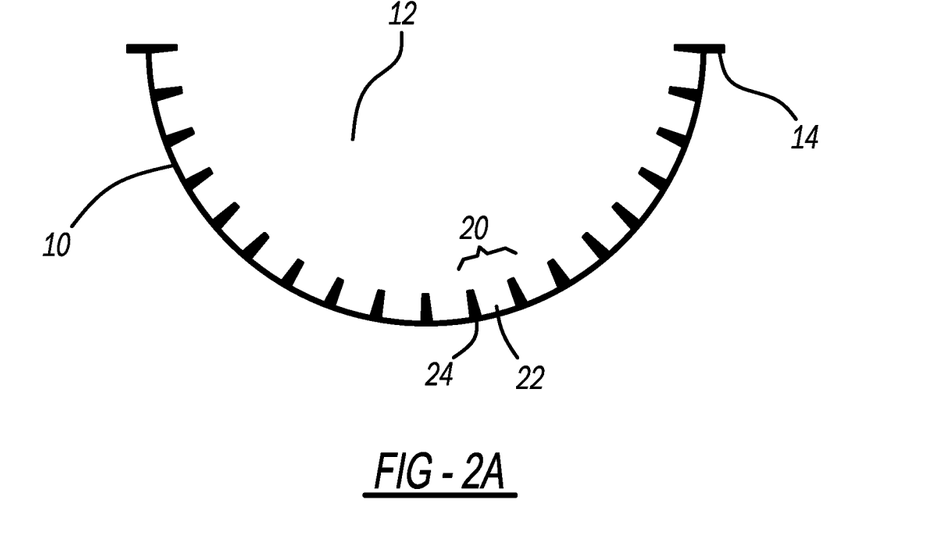
FIGS. 2A and 2B are cross-sectional views of the Descemet constructs shown in FIGS. 1A and 1B, respectively.
Figure 2B:
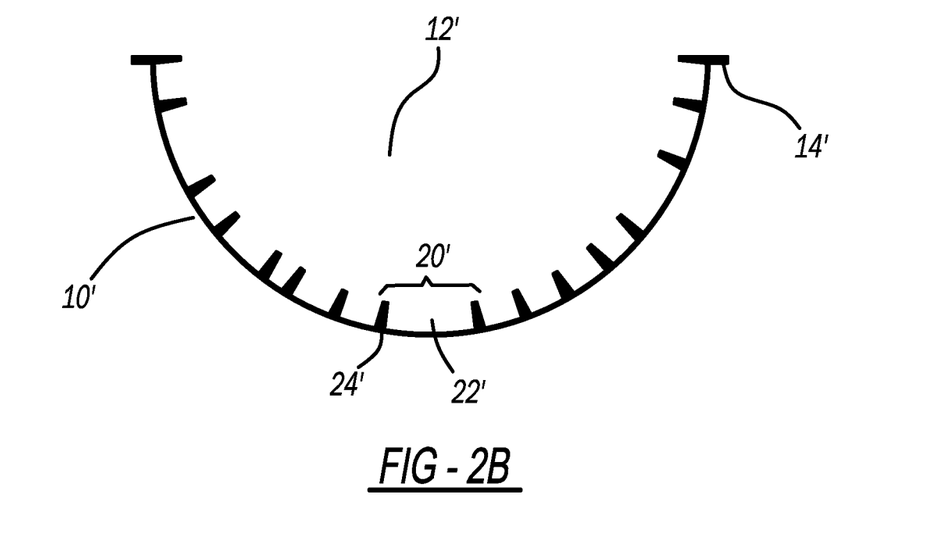

The figures show, schematically and by way of example, the structure of the Descemet construct. In the illustrations in FIGS. 1A and 1B and FIGS. 2A and 2B, the variables are not scaled. On the contrary, the honeycomb-shaped structures are shown enlarged several times in relation to the overall size of the construct. FIGS. 1A and 1B show plan views of the concave side 12 of the dome-shaped Descemet construct according to the invention. FIGS. 2A and 2B show cross-sectional views of the Descemet construct according to FIGS. 1A and 1B, respectively. To illustrate the spatiality of the structure, the honeycomb structures FIGS. 1A and 1B are skewed in perspective toward the edge. The Descemet construct has a basic body 10 in the form of a dome or half-shell, the corresponding ball radius of the dome being adapted to the radius of the cornea in the receiver eye. The honeycomb structure of the microstructuring is composed of imaginary repetitive base elements 20, which each have a central recess 22 and lateral delimits formed as positive webs 24. In the depicted embodiment of the Descemet construct, it has a peripherally protruding edge 14 on the edge side. On the surface of the concave side 12 of the dome-shaped construct 10, a honeycomb structure consisting of repetitive base elements 20, each with depressions 22 and lateral webs 24, is provided. In the illustrated embodiment, a circumferential substantially smooth edge 14 is formed on the upper edge of the dome-shaped base body 10. In a particular variant, as shown in FIGS. 1A and 2A, the honeycomb structure is strictly regular; that is to say, it is constructed from essentially uniform and preferably essentially the same basic elements. In an alternative and preferred variant, as shown in FIGS. 1B and 2B, the honeycomb structure is irregular. That is, the imaginary basic elements each have a different size and/or different individual shape, the sizes of the basic elements being preferably (quasi-) stochastically distributed in the honeycomb structure.

Example 1: Preparation of an Artificial Descemet Construct

1. Lithographic Production of a Matrix

1.1 Two-Photon Lithography

Two-photon lithography (2PL) is based on the physical effect of two-photon absorption (2PA) and allows the production of three-dimensional structures at a lateral resolution of 150 nm and an axial resolution of 400 nm. The widened beam of a femtosecond fiber laser with a wavelength of 780 nm is coupled into an inverted microscope lens and is focused by it into a liquid and photosensitive polymer. Because the laser is focused and pulsed, the focus intensity is high enough to allow two-photon absorption within the focus. In the corresponding region, instead of infrared radiation, ultraviolet radiation with a wavelength of 390 nm is emitted. The liquid photopolymer crosslinks only during the exposure by the energetic UV radiation, so that the liquid polymer cures in the region in which two-photon absorption takes place.

By movement of the photosensitive polymer relative to the focus, any structures of polymer, such as IP-Dip, IP-L, IP-G, OrmoComp, AR-P3120, SUB, can be produced. A final development step a solvent dissolves the unexposed material from the exposed to obtain the structure.

There are four variations of two-photon lithography, each of which can be used to produce relevant structures:
a) In the conventional method, the laser beam is focused through a glass plate into the photosensitive polymer. In addition, the microscope lens and the glass plate are used to introduce an amount of laser light into the polymer to maximize the resolution. The working distance of the objective limits the maximum structural height in this variation of the method. The structure is built up from the top of the substrate.
b) Dip-in laser lithography (DiLL) also allows the use of opaque substrates such as metal or silicon. Here, the laser beam is focused on the underside of the substrate, the photosensitive polymer is located between the microscope objective and the substrate, and simultaneously serves as an immersion medium. The structure is built up from the bottom of the substrate. The maximum structure height due to the piezoelectric control is 300 µm. By using the z-drive of the microscope lens, far higher structures can be realized.
c) The third variation consists in the use of an air lens. This principle corresponds to that of the conventional process, but without the use of immersion oil.
d) With an add-on, which is based on galvoscanners, the simultaneous writing with several foci can increase the writing speed up to 200 fold.

The structures to be manufactured with the 2PL must be programmed first. For this purpose, either the Describe® software (for other systems also Matlab®) that uses the GWL programming language can be used or the corresponding structure can be programmed as a .stl-file and then transferred to the Nanoslicer® program. Since the photosensitive polymer is not suitable as a material for cell differentiation, the inverted structure of the Descemet membrane is prepared and formed into a suitable material. Silicone rubber or human or animal collagen are used. Correspondingly, hexagonal nubs are produced which differ in diameter and height and are randomly arranged.

The procedure for producing the structures is as follows:
fixing the substrate with glue (Fixogum®) in the specimen holder
dropping of the respective photopolymer on the upper side (for the conventional process and the air lens) or the underside (for the DiLL process) of the substrate, respectively
for the conventional method, in addition: application of immersion oil to the underside of the substrate
fixing the sample holder with the sample in the 2PL device
start writing according to the programming of the structure, the sample is moved relative to the focus of the laser according to the programmed structure

1.2 Interference Lithography

In the case of interference lithography, two-beam or multi-beam interference is used to image and store the corresponding interference pattern in a light-sensitive surface. For this purpose, a laser beam (argon ion laser) is expanded and (e.g. by means of a beam splitter cube) into two partial beams. These are superimposed with mirrors (plane or concave mirrors) at a certain angle so that a striped pattern with a certain lattice constant arises as a function of this angle as well as the wavelength used.

The light-sensitive sample, which is positioned in the interference pattern, consists of a substrate (metal, silicon, glass), onto which a smooth layer of photopolymer is deposited by means of spin coating (layer thickness, spin cycle). Here, positive or negative lacquers can be used, where negative lacquers crosslink where they are exposed. In the case of positive lacquers, the unexposed portion of the polymer forms the structure.

To store the stripe-shaped interference pattern in the polymer layer, a sample (substrate with resist layer) is exposed with the interference pattern. A subsequent development step (in the case of positive resists) releases the exposed polymer from the layer. In order to produce hexagonal nubs with this method, the same sample must be exposed three times with the interference pattern, the sample being rotated by 60° after each exposure. After the development step, hexagonal nubs consisting of plastic are used, which can also be used for the impression of the Descemet structure in another material. The procedure is as follows: Coating a substrate with a photopolymer; depending on the polymer, baking the sample on a "hot plate"; positioning the sample at the location of the interference pattern in the optical setup; exposing the sample to the interference pattern three times; rotating the sample by 0° in the same direction after each exposure; and developing the sample in the corresponding developer bath.

1.3 Grayscale Lithography

Grayscale lithography is based on the exposure of a mask whose pattern is stored by the exposure in a photosensitive polymer. Different depths of structure are realized by different gray tones on the mask. Behind the mask, an intensity distribution is formed corresponding to the gray tone distribution on the mask. Using a positive resist, the structure is deepest where the intensity is highest. This relationship is reversed for negative resist materials.

In order to produce the inverted Descemet structure by means of the grayscale lithography, a mask must be designed which maps the structure in gray tones. When using a positive resist material, the contours of the hexagon are bright and darker towards the center. If negative resist material is used, the hexagon on the mask is bright in the middle and becomes darker towards the outside. In order to ensure a planar illumination of the mask, this is positioned perpendicular to the optical axis in a widened and focused laser beam. By focusing, the mask is scaled down on the sample so that the dimensions of the structure are true to the original. Here, the procedure is as follows: Coating a substrate with a photopolymer; depending on the polymer, baking the sample on a "hot plate"; positioning the sample at the location of the interference pattern in the optical setup; exposing the sample to an expanded, focused laser beam that immediately after dilation transcends the gray tone mask; and developing the sample in the corresponding developer.

2. Forming of the Final Biological Descemet Construct

Since the material properties are of great importance for cell differentiation, the lithographically produced structure is formed into a softer material—silicone rubber or animal or human collagen are used—so that the reproduced Descemet structure is formed in that material. To produce an implantable Descemet construct from biocompatible material, a castable collagen composition is used, a patterned mold of polymer is first produced.

Example 2: Preparation of the In Vitro Corneal Endothelial Tissue

Mesenchymal stem cells which had previously been removed from the adipose tissue and isolated are seeded on the artificial Descemet construct prepared according to Example 1 in a cell density of at least $5 \times 10^5$ cells per cm2. For uniform distribution and adhesion the construct is shaken orbitally.

After complete adhesion, the membrane is clamped into a bioreactor (37° C., 5% $CO_2$, 100% rel. humidity) and cultured until the stem cells are completely differentiated and the function of corneal endothelial cells is achieved (testable by endothelial cell-specific markers or by function tests). The cultivation period depends on the differentiation rate of the specific stem cells. For culturing, a basal culture medium containing 10% serum and 1% antibiotics is used.

Upon completion of the cultivation, a fully differentiated de novo corneal endothelial tissue is obtained on the Descemet construct. This tissue adheres to the Descemet construct and, together with the Descemet construct, forms an in vitro implant for repairing a corneal endothelial defect in a recipient eye.

The invention claimed is:

1. An artificial Descemet construct configured to mechanotransductively differentiate biological cells into de novo corneal endothelial tissue, the construct comprising:
    a dome-shaped base body; and
    a honeycomb structure formed on a concave side of the base body,
    wherein the construct comprises a biocompatible polymer, the biocompatible polymer being configured to be both permeable to aqueous humor and at least partially resorbable after implantation into a subject's eye.

2. The artificial Descemet construct according to claim 1, wherein the honeycomb structure comprises repetitive base elements, each base element having a central recess enclosed by lateral webs,
    wherein each lateral web has a height of 0.3 to 1 μm and a width of 1 to 8 μm, and
    wherein each central recess has a width of 10 to 20 μm.

3. The artificial Descemet construct according to claim 2, wherein the repetitive base elements are of substantially equal size.

4. The artificial Descemet construct according to claim 2, wherein the repetitive base elements have different sizes for a quasi-stochastic size distribution of the repetitive base elements in the honeycomb structure.

5. The artifical Descemet construct according to claim 2, wherein the repetitive base elements each have a hexagonal basic shape.

6. The artificial Descemet construct according to claim 1, wherein the construct comprises a biocompatible polymer.

7. The artificial Descemet construct of claim 1, further comprising corneal endothelial tissue disposed on the concave side of the base body, wherein the corneal endothelial tissue is formed from isolated cells.

8. An artificial Descemet construct comprising:
    a polymeric dome-shaped base body having a concave surface; and
    a web of connected walls extending from the concave surface and defining a plurality of recesses, wherein the polymeric dome-shaped base body comprises a biocompatible polymer, the biocompatible polymer being, after implantation into a subject's eye, both permeable to aqueous humor and at least partially resorbable.

9. The artificial Descemet construct according to claim 8, wherein each recess of the plurality has an independent shape selected from the group consisting of a circle, a rectangle, a square, a hexagon, and a pentagon.

10. The artificial Descemet construct according to claim 8, wherein each recess of the plurality has a hexagonal shape such that the web of connected walls defines a honeycomb structure.

11. The artificial Descemet construct according to claim 8, wherein cells are seeded onto the concave surface within the plurality of recesses, the cells being adult stem cells, embryonic stem cell, or induced pluripotent stem cells.

12. The artificial Descemet construct according to claim 8, wherein corneal endothelial cells are disposed the concave surface within the plurality of recesses.

13. The artificial Descemet construct according to claim 8, wherein the concave surface of the polymeric dome-shaped base body has a radius corresponding to a radius of a cornea.

14. The artificial Descemet construct according to claim 8, wherein the polymeric dome-shaped base body is constructed of a material selected from a group consisting of collagen type I, collagen type II, collagen type IV, collagen type VIII, laminin, fibronectin, and combinations thereof.

15. The artificial Descemet construct according to claim 8, further comprising corneal endothelial tissue disposed on the concave surface within the plurality of recesses.

16. An artificial Descemet construct comprising:
a polymeric dome-shaped base body having a concave surface;
a web of connected walls extending from the concave surface and defining a plurality of recesses; and
corneal endothelial tissue disposed on the concave surface within the plurality of recesses,
wherein the polymeric dome-shaped base body comprises a biocompatible polymer, the biocompatible polymer being, after implantation into a subject's eye, both permeable to aqueous humor and at least partially resorbable.

17. The artificial Descemet construct according to claim 8 configured as a prefabricated corneal implant.

* * * * *